United States Patent
Kalveram et al.

(10) Patent No.: US 7,460,222 B2
(45) Date of Patent: Dec. 2, 2008

(54) MEASURING DEVICE FOR THE OPTICAL ANALYSIS OF A TEST STRIP

(75) Inventors: Stefan Kalveram, Viernheim (DE); Friedrich Ziegler, Stuttgart (DE); Hans-Peter Haar, Wiesloch (DE); Hans List, Hesseneck-Kailbach (DE); Jean-Michel Asfour, Offenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 328 days.

(21) Appl. No.: 10/535,647

(22) PCT Filed: Nov. 14, 2003

(86) PCT No.: PCT/EP03/12724

§ 371 (c)(1),
(2), (4) Date: Sep. 29, 2005

(87) PCT Pub. No.: WO2004/048881

PCT Pub. Date: Jun. 10, 2004

(65) Prior Publication Data

US 2006/0098203 A1    May 11, 2006

(30) Foreign Application Priority Data

Nov. 22, 2002  (DE)  .................. 102 54 685

(51) Int. Cl.
*G01N 1/10* (2006.01)
*G01N 21/47* (2006.01)

(52) U.S. Cl. .................. 356/244; 356/445; 356/39; 250/458.1; 422/82.05; 436/164

(58) Field of Classification Search ........... 356/446, 356/39, 435, 436, 444, 244–246, 73; 250/458.1; 436/164; 422/82.05, 50, 82.09
See application file for complete search history.

(56) References Cited

U.S. PATENT DOCUMENTS

| | | | |
|---|---|---|---|
| 6,285,454 B1 | 9/2001 | Douglas et al. | |
| 6,331,438 B1 | 12/2001 | Aylott et al. | |
| 6,955,787 B1 * | 10/2005 | Hanson | 422/50 |
| 2002/0066865 A1 | 6/2002 | Hung | |

(Continued)

FOREIGN PATENT DOCUMENTS

JP    10197526    7/1998

OTHER PUBLICATIONS

Yu, Gang et al. Elsevier Science S.A. "Synthetic Metals" 111-112(2000)133-137.

(Continued)

*Primary Examiner*—L. G Lauchman
(74) *Attorney, Agent, or Firm*—Richard T. Knauer; Roche Diagnsotics Operations, Inc.

(57) ABSTRACT

The invention concerns a measuring device for the optical analysis of a diagnostic test element (10) comprising a light source (16), a photodetector (24) and a device (12) for positioning the test element (10) between the light source (16) and photodetector (24) where the light source (16) has one or several organic light-emitting diodes (OLEDs) and the OLEDs (14) for a composite structure with an imaging optics (20) and/or a photodetector (24) by means of a support substrate.

24 Claims, 2 Drawing Sheets

U.S. PATENT DOCUMENTS

| 2002/0123671 | A1 | 9/2002 | Haaland |
| 2003/0010892 | A1* | 1/2003 | Clark ................ 250/208.1 |
| 2003/0035109 | A1 | 2/2003 | Hartwich et al. |
| 2005/0046847 | A1* | 3/2005 | Cromwell et al. ........ 356/417 |

OTHER PUBLICATIONS

Zou, L. et al. XP-002288691 "Combinatorial fabrication and studies of 4, 4'-bis(9-carbozolyl) biphenyl (CBP)-based UV-violet OLED arrays", Organic Light-Emitting Materials and Devices V, Zakya H. Kafafi, Editor, Proceedings of SPIE vol. 4464 (2002) 197-202.

Johnson, S. XP002288692 "Sensible Sensors The beauty of a new chemical sensor lies in its simplicity", Insider, Newsletter for employees of Ames Laboratory, vol. 13, No. 3, Mar. 2002 (3pp).

Mikhael, M.G., et all, "Self-Healing Flexible Photonic Composites for Light Sources", Society of Vacuum Coasters, 45th Annual Technical conference Proceedings, Apr. 13-18, 2002, ISSN: 0737-5921; pp. 530-534.

* cited by examiner

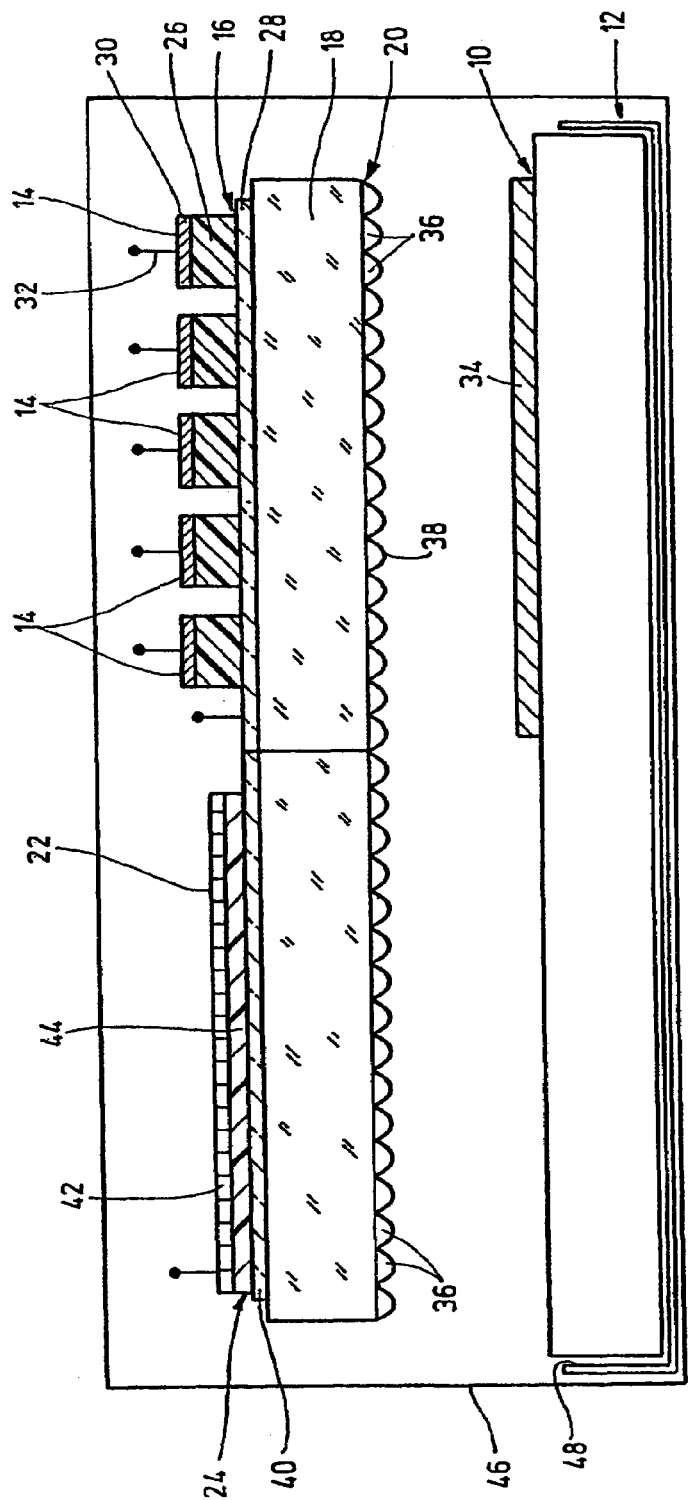
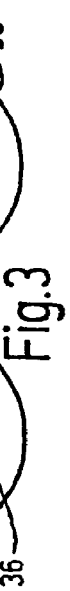
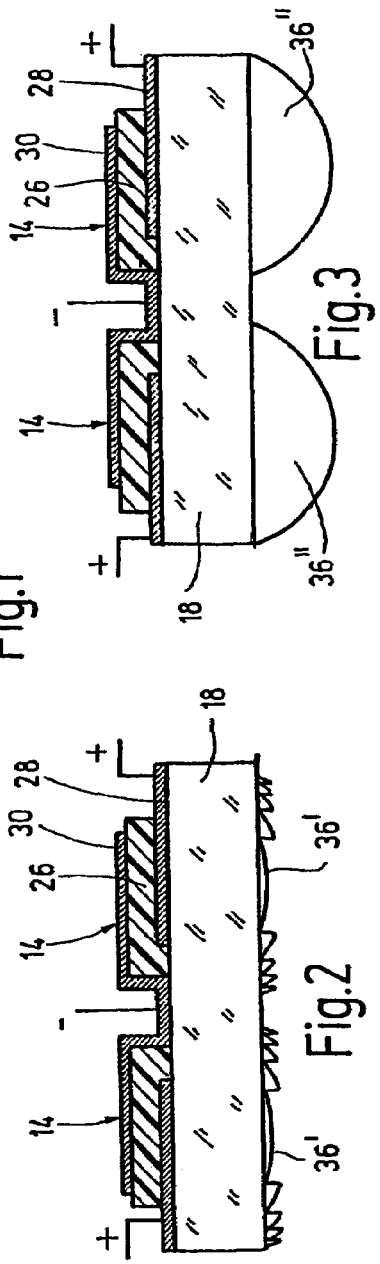
Fig.1
Fig.2
Fig.3

MEASURING DEVICE FOR THE OPTICAL ANALYSIS OF A TEST STRIP

The invention concerns a measuring device for the optical analysis of especially a test element diagnostic test element comprising a light source, a photodetector and a device for positioning the test element in an optical path between the light source and photodetector.

Analytical systems of this type are used in medical diagnostics in order to optically examine a disposable test strip that can be loaded with an analyte for example for colour changes. The photometric arrangement that is required for this in a measurement module that may be used by the test subject himself requires an exact orientation of the individual components in order to achieve the desired performance. In the manufacturing process the light source, optical system and detector are usually assembled in large numbers by so-called pick and place processes. This can only be carried out with a limited degree of accuracy and reproducibility and becomes the more time-consuming the smaller the components are and the smaller the optical manufactured size and focal length that is available.

In the case of display elements in electronic devices it is known that display pixels can be formed on the basis of organic light-emitting diodes (OLED) which in contrast to conventional inorganic LEDs that are based on crystalline semi-conductor structures, can be manufactured over a large area as very thin flexible flat emitters.

On this basis the object of the invention is to improve a measuring device of the type described above and in particular to achieve a simple compact design with a high manufacturing and measuring precision.

The combination of features stated in claim 1 are proposed to achieve this object. Advantageous embodiments and further developments of the invention are derived from the dependent claims.

The basis of the invention is the idea of creating a solid composite of light source, optical system and/or detector. Accordingly the invention proposes that the light source has one or more organic light-emitting diodes (OLEDs) and the OLEDs form a composite structure over a support substrate with an imaging optical system and/or the photodetector.

This allows a simplified batchwise manufacture with a high, uniform positioning precision of the components and a low manufacturing variation. The manufactured size can be considerably reduced due to the planar construction of at least the light source. The use of OLEDs gives rise to a wide variety of advantages such as high luminosity with a relatively low energy consumption, wide viewing angle, potentially low manufacturing costs and reduction of material costs and a production process that can be automated on a large scale to manufacture photometric modules for analyzers.

The use of OLEDs gives rise to further unexpected advantages compared to conventional LED light sources in photometric measuring units: It is possible to vary the design of the light source which can be optimized for the photometric arrangement. As a result of the homogeneous light distribution over the OLED surface, the imaging optics can be improved without requiring an adaptation with regard to shadowing electrodes as would be the case for conventional LEDs. The substantial lower tolerances in the distance between the optical system and light source and in the lateral positioning accuracy makes it more possible to collimate the measuring light in order to illuminate the test field in a manner which is substantially independent of distance. Even if it is not possible to achieve a perfect collimation, there is at least a lower sensitivity towards distance tolerances.

Moreover, the low positioning tolerance in the composite structure allows a small focal length which enables a more efficient operation. In particular this allows measurement on the emitter side with a low power requirement or an improved signal-to-noise-ratio on the receiver side.

Advantageously a plurality of OLEDs are arranged on the support substrate as a one-dimensional or two-dimensional light-emitting pixel array. In this connection the OLEDs can have different emission wavelength ranges and/or preferably be aligned in a grid-like manner on different lighting target areas. This enables a spatially resolved lighting in order to localize the target area for example in the case of microscopic quantities of sample or to carry out additional analyses.

The OLEDs can be constructed in one-dimensional compactness from two electrode layers and a sandwich-like intermediate electroluminescent light-emitting layer that is preferably formed from a polymer material. This enables a pixel size of less than 500 µm, preferably less than 200 µm to be achieved.

An advantageous embodiment envisages that the OLEDs have a transparent front electrode layer adjoining the substrate for radiating light through the substrate and a rear electrode layer that faces away from the substrate. In this connection the front or the rear electrode layer can be formed or contacted jointly for all OLEDs while individual pixels can be separately controlled by a single electrode opposing each pixel.

The imaging optics preferably has at least one optical lens to form an image of the light source on a target area of the test element and/or an image of a target area of the test element on the photodetector.

For a further integration it is advantageous when the imaging optics has a plurality of microstructured, preferably aspherical lens units in a two-dimensional arrangement. This imaging optics is preferably formed by a lens structure moulded on the support substrate especially by embossing. Alternatively it is also possible that the imaging optics is formed by a foil material, preferably a polymer-based foil material having a lens structure that is preformed especially by embossing (hot stamping or injection stamping), injection moulding or reaction moulding that is joined to the support substrate in a planar fashion.

A compact structure with a favourable optical path is achieved by arranging the OLEDs on one side of the support substrate and the imaging optics on the opposite side of the support substrate. The support substrate should consist of a transparent flat material especially of a thin glass or a polymer film.

Another preferred embodiment of the invention envisages that the photodetector is formed by at least one layer-shaped organic photodiode. This further improves the positioning of the optical components where the layered deposition of light emitter and receiver is also advantageous with regard to an integrated manufacture.

A plurality of organic photodiodes are advantageously arrayed on the support substrate as a linear or planar sensor pixel array to enable a spatially resolved scanning. In another advantageous embodiment a plurality of OLEDs and photodiodes that are locally combined as an elementary photometer and are arranged as a matrix on a surface of the support substrate, form a multiple photometer.

Another improvement provides that the device for positioning comprises a holder, a guide or a stop for the test element. The device for positioning can also comprise a test element holder that can be moved between a loading position and a measuring position.

In order to increase the durability it is advantageous when the surface of the OLEDs is screened from the environment in a material-tight manner by a coating or housing.

Another advantageous embodiment provides that the test element is formed by a test strip provided with optically scannable indicator fields for biological substances to be detected and especially a test strip designed as a disposable article for example a glucose test strip.

The invention is further elucidated in the following on the basis of an embodiment shown in a schematically simplified manner in the drawing.

FIG. 1 shows a photometric measuring device as a composite structure of organic light-emitting diodes and photodiodes as well as imaging optics for analysing diagnostic test strips in a sectional drawing;

FIGS. 2 and 3 show further embodiments of organic light-emitting diodes and their associated imaging optics in cross-section;

Figure 4:
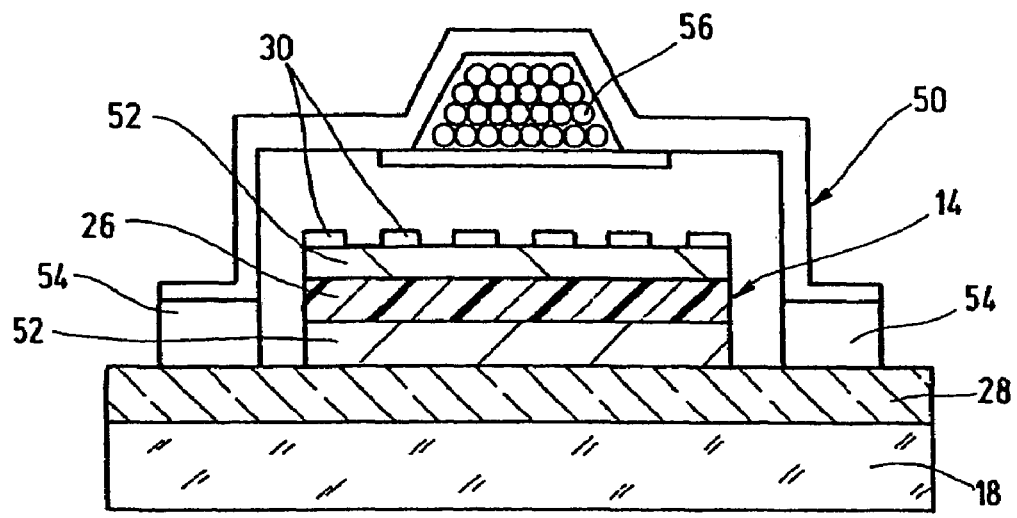
FIG. 4 shows a hermetically screened organic light-emitting diode arrangement in a housing in cross-section and FIG. 5 shows a matrix arrangement of single photometers based on combined organic light-emitting diodes and photodiodes in a top-view.

The optical measuring device shown in the diagram serves to photometrically analyse or evaluate diagnostic test strips 10, for example for glucose tests in blood samples. It comprises a positioning unit 12 for the test strips 10 and a composite structure consisting of a light source 16 formed by at least one organic light-emitting diode (OLED 14), a support substrate 18, an imaging optics 20 and a photodetector 24 having at least one polymer photodiode 22.

In the embodiment shown in FIG. 1 several OLEDs 14 arranged in a matrix-like manner are provided which have different emission wavelengths. The film-like OLEDs 14 are based on at least one thin organic light-emitting layer 26 which is arranged in a sandwich formation between two electrode layers 28, 30. When a voltage is applied, positive charges are displaced from the anode layer 28 into the light-emitting layer 26, while electrons are injected onto the cathode layer 30. As a result of the electrical field, the injected charge carriers each move to the opposite electrode layer. If electrons and holes meet, electron-hole pairs are formed which can recombine while emitting radiation. The emission spectrum is determined by the organic semiconductor material that is used. Highly efficient OLEDs contain further injection and transport layers to optimize this injection electroluminescent effect and auxiliary layers as diffusion barriers and for homogenization.

In the embodiment of FIG. 1 a common anode 28 adjoining the support substrate 18 is provided which is composed of ITO (indium-tin-oxide) or related oxidic compounds as well as conducting polymers and is permeable to the emitted light. In contrast the cathodes 30 consisting of a metal layer can be individually controlled by separate pick-ups 32.

The different wavelengths of the controlled OLEDs enable different optically detectable reactions or properties of the analytical test areas 34 to be evaluated on the test strip 10. In addition the matrix arrangement of the OLEDs enables different illumination target areas or illumination spots to be irradiated in order to for example examine very small sample volumes on a given test area 34 in a spatially resolved manner.

The support substrate 18 is composed of a thin flat material that is permeable to the generated light and in particular a thin glass or flexible polymer film or a suitable multilayer. The OLEDs 14 that are mounted thereon can be manufactured as layer emitters in extremely small dimensions. For example the pixel size can be between 50 and 200 μm whereas the layer thickness of the light-emitting layer 26 can be in the range of 100 nm. Such structures can be produced with high precision by a variety of process techniques such as dipping methods, spin and dip coating, sieve and inkjet printing, PVD and CVD methods.

The imaging optics 20 is mounted on the side of the support substrate 18 that is opposite to the OLEDs 14. It has a plurality of two-dimensionally distributed lens units 36 to couple out the measuring light on the emitter side and couple in the measuring light on the detector side. They can be laminated onto the side of the substrate facing the test element 10 as a prefabricated microstructured lens structure 38 for example in the form of a hot-stamped film material. Alternatively the lens structure can be directly moulded onto the free substrate side for example by embossing.

Like the OLEDs the polymer photodiode 22 is a sandwich structure composed of two electrode layers 40, 42 and a semiconducting polymer layer 44. Such photo-sensitive layer cells are known and described for example in the publication of Dey et al., *A dye/polymer based solid state thin film photoelectrochemical cell used for light detection*, Synthetic Metals 118 (2001), p. 19-23 the contents of which are hereby incorporated.

Instead of a single photodiode 22, it is also possible for a plurality of photodiodes to be arranged on the support substrate 18 as a one-dimensional or two-dimensional array or diode field. It is also conceivable that a conventional photometric receiver is combined with an OLED light source as described above.

The composite structure comprising OLED 14, imaging optics 20 and photodiode 22 enables a very compact and optically precise photometer arrangement to be achieved which can be provided to the user in a compact housing 46 in order that he himself may evaluate test strips 10 that are in particular designed as disposable articles. For this purpose a holder 48 that can be inserted into the housing 46 is provided as a positioning unit for the test strip 10.

In the arrangement of FIG. 1 the optical path extends from the light source 16 through the substrate 18 and the imaging optics 20 onto the test area 34 and is reflected or remitted there via the imaging optics 20 through the substrate 18 into the detector 24. However, a transmissive arrangement is also basically possible in which the test strip 10 is examined in the transmitted light between the light source and detector.

According to FIG. 1 an image of each OLED 14 is formed on a target area on the test strip 10 by a group of lens units 36. The embodiments shown in FIGS. 2 and 3 differ therefrom essentially in that each OLED 14 has an associated single lens 36 with a large lens diameter. According to FIG. 2 this is designed as a Fresnel lens 36' and its design is optimized for microstructuring and moulding technology. FIG. 3 shows an aspherical collecting lens 36" for focussing the emitted light.

In the embodiment of FIGS. 2 and 3 special anode layers of the OLEDs 14 are provided as individually controllable front electrodes while a continuous cathode layer 30 forms a common rear electrode.

In the embodiment example shown in FIG. 4 a housing 50 is provided for hermetically screening the free surface of the OLED 14 from the environment in order to protect the organic light-emitting layer 26 as well as the transport/injection layers 52 and metal electrodes 30 from oxidation by oxygen and from the effects of moisture. The edge of the housing 50 can be attached to the electrode layer 28 or the support substrate 18 by an adhesive layer 54 and the housing can contain a desiccant 56 as an additional protection against moisture. It is obvious that a layer or similar means can be provided together with the support substrate 18 as a material-tight barrier instead of a separate housing.

Figure 5:
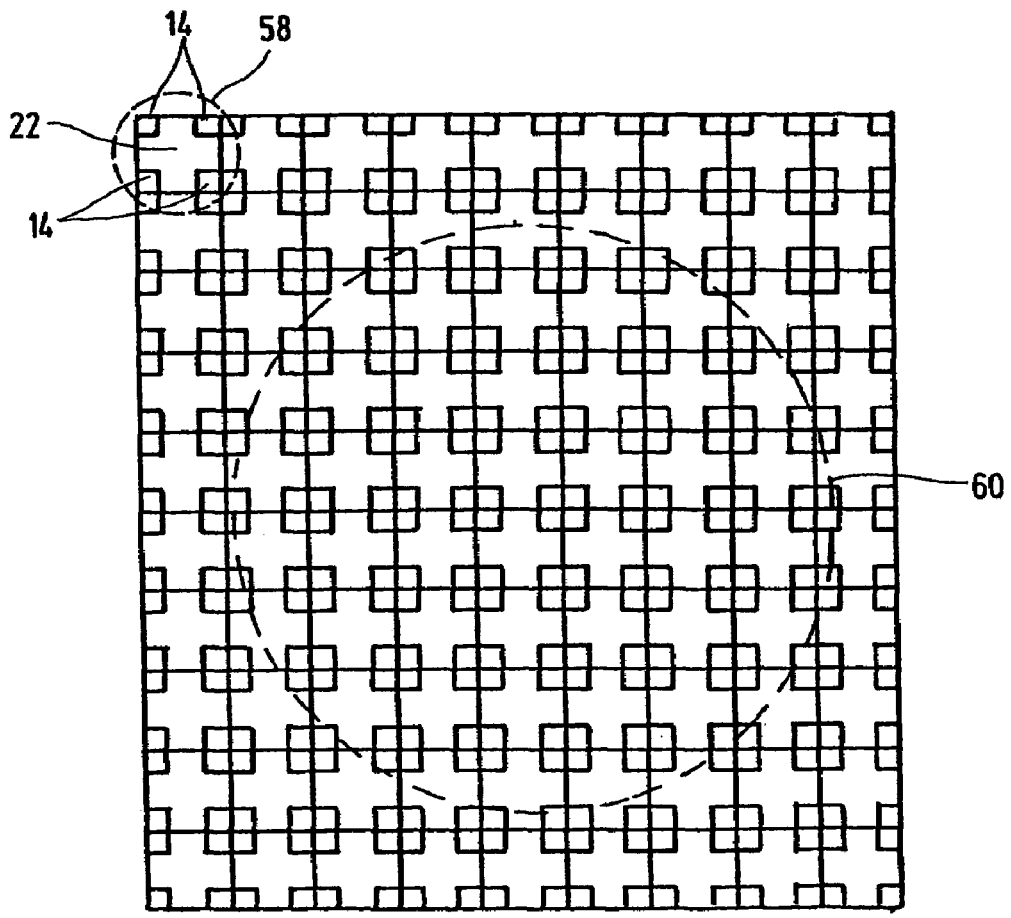

A further embodiment is shown in FIG. 5 with a plurality of elementary photometers 58 arranged on the surface of the support substrate in a matrix-like manner. Each of the elementary photometers 58 are formed on a quadratic pixel area by a cross-shaped polymer photodiode 22 and four OLEDs 14 arranged in the corner areas that operate with different wavelengths where of course other local combinations are also possible. This allows a target area on the test element 10 to be optically scanned in a spatially resolved manner as illustrated in FIG. 5 by the circle 60. This allows small amounts of sample to be photometrically analysed even when the positioning is inaccurate. At the same time it also enables the optical measuring path to be reduced and optionally allows one to even dispense with an imaging optics.

What is claimed is:

1. A measuring device for optically analyzing a diagnostic test element, the measuring device comprising:
a light source having at least one organic light-emitting diode;
imaging optics;
a photodetector; and
a device adapted to position the test element in an optical path between the light source and the photodetector, wherein the light source forms a composite structure including a support substrate, the imaging optics and the photodetector, and wherein the support substrate is transparent.

2. The measuring device of claim 1 wherein the support substrate is formed of a transparent material selected from the group consisting of glass and a multilayerpolymer film.

3. The measuring device of claim 1 wherein a plurality of organic light-emitting diodes are arranged on the support substrate as a one-dimensional or two-dimensional light-emitting pixel array.

4. The measuring device of claim 3 wherein the organic light-emitting diodes have emission wavelength ranges that are different from one another.

5. The measuring device of claim 3 wherein the organic light-emitting diodes are aligned in a grid-like manner on different illumination target areas.

6. The measuring device of claim 1 wherein the at least one organic light-emitting diode includes two electrode layers and an intermediate sandwich-like electroluminescent light-emitting layer that is formed from a polymer.

7. The measuring device of claim 1 wherein the at least one organic light-emitting diode has a pixel size of less than 500 µm.

8. The measuring device of claim 1 wherein the at least one organic light-emitting diode has a pixel size of less than 200 µm.

9. The measuring device of claim 1 wherein the at least one organic light-emitting diode has a transparent front electrode layer adjoining the support substrate and a rear electrode layer facing away from the substrate.

10. The measuring device of claim 1 wherein the imaging optics has at least one optical lens formed to form an image of the light source on a target area of the test element.

11. The measuring device of claim 1 wherein the imaging optics has at least one optical lens formed to form an image of the light source on the photodetector.

12. The measuring device of claim 1 wherein the imaging optics has a plurality of microstructured, aspherical lens units in a two-dimensional arrangement.

13. The measuring device of claim 1 wherein the imaging optics is formed by a lens structure molded onto the support substrate by embossing.

14. The measuring device of claim 1 wherein the imaging optics is formed by a polymer-based foil material having a lens structure that is joined to the support substrate in a planar fashion.

15. The measuring device of claim 1 wherein the at least one organic light-emitting diode is arranged on one side of the support substrate and the imaging optics are arranged on an opposite side of the support substrate.

16. The measuring device of claim 1 wherein the photodetector is formed by at least one layer-shaped organic photodiode.

17. The measuring device of claim 16 wherein a plurality of organic photodiodes are arranged on the support substrate as a linear or a planar sensor pixel array.

18. The measuring device of claim 16 wherein the at least one organic light-emitting diode and the at least one photodiode are applied to the support substrate by a coating process.

19. The measuring device of claim 16 wherein a plurality of organic light-emitting diodes and photodiodes are locally combined as elementaiy photometers and are arranged as a matrix on a surface of the support substrate to form a multiple photometer.

20. The measuring device of claim 1 wherein the positioning device includes a holder, a guide or a stop for the test element.

21. The measuring device of claim 1 wherein a surface of the at least one organic light-emitting diode is screened from the environment in a material-tight manner by a coating or a housing.

22. The measuring device of claim 1 wherein the test element is formed by a test strip provided with optically scannable indicator fields for biological substances to be detected and designed as a disposable article.

23. An optical measuring device formed to photometrically analyze a diagnostic test strip, the device comprising:
a positioning unit for the test strip; and
a composite structure including a light source formed by an organic light-emitting diode, an imaging optics, a photodetector having a polymer photodiode, and a transparent support substrate formed to support the light source, imaging optics, and the photodetector.

24. A measuring device for optically analyzing a diagnostic test element, the measuring device comprising:
a light source having at least one organic light-emitting diode;
a photodetector; and
a device formed to position the test element in an optical path between the light source and the photodetector, wherein the light source forms a composite structure including a transparent support substrate and the photodetector.

* * * * *